12) United States Patent
Ramella-Roman (10) Patent No.: US 10,791,983 B2
(45) Date of Patent: Oct. 6, 2020

(54) OPTICAL IMAGING FOR PRETERM BIRTH ASSESSMENT

(71) Applicant: Jessica Ramella-Roman, Miami, FL (US)

(72) Inventor: Jessica Ramella-Roman, Miami, FL (US)

(73) Assignee: The Florida International University Board of Trustees, Miami, FL (US)

(*) Notice: Subject to any disclaimer, the term of this patent is extended or adjusted under 35 U.S.C. 154(b) by 820 days.

(21) Appl. No.: 15/468,763

(22) Filed: Mar. 24, 2017

(65) Prior Publication Data

US 2018/0271430 A1 Sep. 27, 2018

(51) Int. Cl.
*A61B 5/00* (2006.01)
*A61B 5/1455* (2006.01)

(52) U.S. Cl.
CPC .......... *A61B 5/435* (2013.01); *A61B 5/0066* (2013.01); *A61B 5/14558* (2013.01)

(58) Field of Classification Search
CPC .... A61B 5/435; A61B 5/14558; A61B 5/0066
See application file for complete search history.

(56) References Cited

U.S. PATENT DOCUMENTS

2015/0080744 A1* 3/2015 Li .................... A61B 5/435
600/478

OTHER PUBLICATIONS

Goldenberg et al., "Epidemiology and causes of preterm birth," Lancet, Jan. 5, 2008, pp. 75-84, vol. 371.
Esplin, "Preterm birth: a review of genetic factors and future directions for genetic study," Obstetrical and Gynecological Survey, Dec. 2006, pp. 800-806, vol. 61, No. 12.
Hamilton et al., "Births: preliminary data for 2015," National Vital Statistics Reports, Jun. 2, 2016, pp. 1-15, vol. 65, No. 3.
Bloomfield, "How is maternal nutrition related to preterm birth," Annual Review of Nutrition, May 2011, pp. 235-261, vol. 31.
Word et al., "Dynamics of cervical remodeling during pregnancy and parturition: mechanisms and current concepts," Seminars in Reproductive Medicine, Jan. 2007, pp. 69-79, vol. 25, No. 1.

(Continued)

*Primary Examiner* — Joel Lamprecht
(74) *Attorney, Agent, or Firm* — Saliwanchik, Lloyd & Eisenschenk (57) ABSTRACT

Methods, apparatuses, and systems for measuring collagen organization in the cervix, assessing the health of a woman's cervix (including a pregnant woman's cervix), characterizing the composition and structure of cervical tissue, and measuring preterm labor risk are provided. Polarization sensitive techniques and properties of cervical tissue, including birefringence, can be used. A method can include acquiring in vivo images of cervical tissue, applying Mueller matrix (MM) polarimetry (including 4×4 Mueller matrix polarimetry), and determining one or more parameters of the cervical tissue using the Mueller matrix (MM) polarimetry. The in vivo images can be analyzed and various parameters that characterize the cervical tissue can be determined. Graphs and maps of the cervical tissue can be generated for use as care provider tools.

14 Claims, 6 Drawing Sheets

(56) References Cited

OTHER PUBLICATIONS

Reiter et al., "Digital examination and transvaginal scan—competing or complementary for predicting preterm birth," Acta Obstetricia et Gynecologica Scandinavica, Apr. 2012, pp. 428-438, vol. 91.

Daskalakis et al., "Fetal fibronectin as a predictor of preterm birth," Journal of Obstetrics and Gynaecology, Jul. 2000, pp. 347-353, vol. 20, No. 4.

Albers, "Monitoring the fetus in labor: evidence to support the methods," Journal of Midwifery and Women's Health, Nov./Dec. 2001, pp. 366-373, vol. 46, No. 6.

Thacker et al., "Continuous electronic heart rate monitoring for fetal assessment during labor," The Cochrane Database of Systematic Reviews, Apr. 2001, pp. 1-6, No. 2.

Kleissl et al., "Collagen changes in the human uterine cervix at parturition," American Journal of Obstetrics and Gynecology, Apr. 1, 1978, pp. 748-753, vol. 130, No. 7.

Granstrom et al., "Changes in the connective tissue of corpus and cervix uteri during ripening and labour in term pregnancy," British Journal of Obstetrics and Gynaecology, Oct. 1989, pp. 1198-1202, vol. 96.

Anastasiadou et al., "Polarimetric imaging for the diagnosis of cervical cancer," Physica Status Solidi (C), Mar. 2008, pp. 1423-1426, vol. 5, No. 5.

Dillet et al., "Size determination by use of two-dimensional mueller matrices backscattered by optically thick random media," Applied Optics, Jul. 2006, pp. 4669-4678, vol. 45, No. 19.

Lu et al., "Interpretation of mueller matrices based on polar decomposition," Journal of the Optical Society of America A, May 1996, pp. 1106-1113, vol. 13, No. 5.

Gan et al., "Dispersion analysis of collagen fiber networks in cervical tissue using optical coherence tomography," Photonic Therapeutics and Diagnostics XII, May 2016, vol. 9689, Abstract.

Garfield et al., "Methods and devices for the management of term and preterm labor," Annals of the New York Academy of Sciences, Sep. 2001, pp. 203-224, vol. 943.

Pierangelo et al., "Polarimetric imaging of uterine cervix: a case study," Optics Express, Jun. 5, 2013, pp. 14120-14130, vol. 21, No. 12.

Bai et al., "Dynamic multicomponent engineered tissue reorganization and matrix deposition measured with an integrated nonlinear optical microscopy-optical coherence microscopy system," Journal of Biomedical Optics, Mar. 2014, pp. 036014-1-036014-10, vol. 19, No. 3.

Soleimani et al., "Long-term neurodevelopmental outcomes after preterm birth," Iran Red Crescent Medical Journal, Jun. 5, 2014, pp. 1-8, vol. 16, No. 6.

Saiga et al., "An overview of mortality and sequelae of preterm birth from infancy to adulthood," Lancet, Jan. 19, 2008, pp. 261-269, vol. 371.

Kemp et al., "Preterm birth, infection, and inflammation advances from the study of animal models," Reproductive Sciences, Jul. 2010, pp. 619-628, vol. 17, No. 7.

Kozuki et al., "The associations of birth intervals with small-for-gestational-age, preterm, and neonatal and infant mortality: a meta-analysis," BMC Public Health, Sep. 2013, pp. 1-9, vol. 13, No. 3.

Tielsch et al., "Global Incidence of preterm birth," Low-Birthweight Baby: Born Too Soon or Too Small, Nestle Nutrition Institute Workshop Series, Jun. 19, 2015, pp. 9-15, vol. 81.

Iams et al., "The length of the cervix and the risk of spontaneous premature delivery," The New England Journal of Medicine, Feb. 29, 1996, pp. 567-572, vol. 334, No. 9.

Feltovich et al., "Quantitative ultrasound assessment of cervical microstructure," Ultrasonic Imaging, Jul. 2010, pp. 131-142, vol. 32, No. 3.

Nold et al., "Inflammation promotes a cytokine response and disrupts the cervical epithelial barrier: a possible mechanism of premature cervical remodeling and preterm birth," American Journal of Obstetrics and Gynecology, Mar. 2012, pp. 1-7, vol. 206, No. 208.

Zarko et al., "Continuous cardiotocography (CTG) as a form of electronic fetal monitoring (EFM) for fetal assessment during labour," Cochrane Database of Systematic Reviews, May 2013, pp. 1-136, No. 5.

Honest et al., "Accuracy of cervicovaginal fetal fibronectin test in predicting risk of spontaneous preterm birth: systematic review," The BMJ, Aug. 2002, pp. 40-63.

Berghella et al., "Cervical assessment by ultrasound for preventing preterm delivery," Cochrane Database of Systematic Reviews, Jan. 2013, pp. 1-37, No. 1.

Zork et al., "A systematic evaluation of collagen crosslinks in the human cervix," American Journal of Obstetrics and Gynecology, Mar. 2015, pp. 1-20, vol. 212, No. 3, Author Manuscript.

Fernandez et al., "Investigating the Mechanical Function of the Cervix during Pregnancy using Finite Element Models derived from High Resolution 3D MRI," Computer Methods in Biomechanics and Biomedical Engineering, Mar. 2016, pp. 1-29, vol. 19, No. 4, Author Manuscript.

Akins et al., "Second harmonic generation imaging as a potential tool for staging pregnancy and predicting preterm birth," Journal of Biomedical Optics, Mar./Apr. 2010, pp. 026020-1-026020-10, vol. 15, No. 2.

Read et al., "Cervical remodeling during pregnancy and parturition: molecular characterization of the softening phase in mice," Reproduction, Jul. 2007, pp. 327-340, vol. 134.

Ito et al., "The change in solubility of type I collagen in human uterine cervix in pregnancy at term," Biochemical Medicine, Jun. 1979, pp. 262-270, vol. 21.

Canty et al., "Procollagen trafficking, processing and fibrillogenesis," Journal of Cell Science, Apr. 2005, pp. 1341-1353, vol. 118, No. 7.

Sennstrom et al., "Human cervical ripening, an inflammatory process mediated by cytokines," Molecular Human Reproduction, Apr. 2000, pp. 375-381, vol. 6, No. 4.

Osmers et al., "Glycosaminoglycans in cervical connective tissue during pregnancy and parturition," Obstetrics and Gynecology, Jan. 1993, pp. 88-92, vol. 81, No. 1.

Straach et al., "Regulation of hyaluronan expression during cervical ripening," Glycobiology, Jan. 2005, pp. 55-65, vol. 15, No. 1.

Romero et al., "The preterm parturition syndrome," BJOG: An International Journal of Obstetrics and Gynaecology, Dec. 2006, pp. 17-42, vol. 113.

Aspden, "Collagen organisation in the cervix and its relation to mechanical function," Collagen and Related Research, Mar. 1988, pp. 103-112, vol. 8.

Zhang et al., "A compact fiber-optic SHG scanning endomicroscope and its application to visualize cervical remodeling during pregnancy," Proceedings of the National Academy of Sciences, Aug. 7, 2012, pp. 12878-12883, vol. 109, No. 32.

Chen et al., "Second harmonic generation microscopy for quantitative analysis of collagen fibrillar structure," Nature Protocols, Mar. 2012, pp. 1-43, vol. 7, No. 4, Author Manuscript.

Myers et al., "Changes in the biochemical constituents and morphologic appearance of the human cervical stroma during pregnancy," European Journal of Obstetrics & Gynecology and Reproductive Biology, Jan. 2009, pp. S82-S89, vol. 144S.

Nazac et al., "Optimization of picrosirius red staining protocol to determine collagen fiber orientations in vaginal and uterine cervical tissues by mueller polarized microscopy," Microscopy Research and Technique, Jun. 2015, pp. 1-8, vol. 78, No. 8.

Lee et al., "Optical diagnosis of cervical intraepithelial neoplasm (CIN) using polarization-sensitive optical coherence tomography," Optics Express, Feb. 18, 2008, pp. 2709-2719, vol. 16, No. 4.

Bancelin et al., "Determination of collagen fiber orientation in histological slides using mueller microscopy and validation by second harmonic generation imaging," Optics Express, Sep. 22, 2014, pp. 22561-22574, vol. 22, No. 19.

Collier et al., "Sources of scattering in cervical tissue: determination of the scattering coefficient by confocal microscopy," Applied Optics, Apr. 10, 2005, pp. 2072-2081, vol. 44, No. 11.

(56) References Cited

OTHER PUBLICATIONS

Carlson et al., "Confocal microscopy: imaging cervical precancerous lesions," Gynecologic Oncology, Dec. 2005, pp. S84-S88, vol. 99, No. 3.

Pierangelo et al., "Multispectral mueller polarimetric imaging detecting residual cancer and cancer regression after neoadjuvant treatment for colorectal carcinomas," Journal of Biomedical Optics, Apr. 2013, pp. 046014-1-046014-9, vol. 18, No. 4.

Wood et al., "Polarized light propagation in multiply scattering media exhibiting both linear birefringence and optical activity: Monte Carlo model and experimental methodology," Journal of Biomedical Optics, Jan./Feb. 2007, pp. 014029-1-014029-10, vol. 12, No. 1.

Ghassemi et al., "A new approach for optical assessment of directional anisotropy in turbid media," Journal of Biophotonics, Jan. 20, 2015, pp. 1-9.

Ghassemi et al., "Out-of-plane stokes imaging polarimeter for early skin cancer diagnosis," Journal of Biomedical Optics, Jul. 2012, pp. 076014-1-076014-9, vol. 17, No. 7.

Ramella-Roman et al., "Design, testing, and clinical studies of a handheld polarized light camera," Journal of Biomedical Optics, Nov./Dec. 2004, pp. 1305-1310, vol. 9, No. 6.

Ramella-Roman et al., "Spectroscopic sensitive polarimeter for biomedical applications," Journal of Biomedical Optics, Apr. 2011, pp. 047001-1-047001-7, vol. 16, No. 4.

Ghassemi et al., "A polarized multispectral imaging system for quantitative assessment of hypertrophic scars," Biomedical Optics Express, Oct. 1, 2014, pp. 3337-3354, vol. 5, No. 10.

Drezek et al., "Understanding the contributions of NADH and collagen to cervical tissue fluorescence spectra: modeling, measurements, and implications," Journal of Biomedical Optics, Oct. 2001, pp. 385-396, vol. 6, No. 4.

Gan et al., "Analyzing three-dimensional ultrastructure of human cervical tissue using optical coherence tomography," Biomedical Optics Express, Apr. 1, 2015, pp. 1090-1108, vol. 6, No. 4.

Foxman et al., "Use of the fetal fibronectin test in decisions to admit to hospital for preterm labor," Clinical Chemistry, Feb. 2004, pp. 663-665, vol. 50, No. 3.

Myers et al., "The mechanical role of the cervix in pregnancy," Journal of Biomechanics, Jun. 25, 2015, pp. 1-29, vol. 48, No. 9, Author Manuscript.

Iams et al., "Care for women with prior preterm birth," American Journal of Obstetrics and Gynecology, Aug. 2010, pp. 1-21, vol. 203, No. 2, Author Manuscript.

Bishop, "Pelvic scoring for elective induction," Obstetrics and Gynecology, Aug. 1964, pp. 266-268, vol. 24, No. 2.

Vink et al., "Cervical etiology of spontaneous preterm birth," Seminars in Fetal and Neonatal Medicine, Apr. 2016, pp. 1-17, vol. 21, No. 2, Author Manuscript.

Stoff et al., Cervical Collagen Imaging for Determinign Preterm Labor Risks Using a Colposcope with Full Mueller Matrix Capability, Proc. SPIE 9689, Photonic Therapeutics and Diagnostics XII, 968947, Mar. 8, 2016.

* cited by examiner

OPTICAL IMAGING FOR PRETERM BIRTH ASSESSMENT

BACKGROUND OF THE INVENTION

Preterm birth (PTB) is defined as the delivery of a baby prior to 37 weeks of gestation. PTB is the number one cause of infant death worldwide. It is also the number one cause of infant neurological disorders, long-term cognitive impairment, and leads to health issues related to hearing, vision, digestion, and breathing. Numerous factors including infection, inflammation, vascular disease, short intervals between pregnancies, multiple gestations and genetic factors lead to PTB. In the United States, PTB occurs in over 11% of births while in the developing world the incidence of PTB is over 15%. To decrease preterm births, it is important to identify at risk pregnancies to initiate preventive interventions.

BRIEF SUMMARY

Embodiments of the present invention include methods, apparatuses, and systems for measuring collagen organization in the cervix, assessing the health of a woman's cervix (including a pregnant woman's cervix), characterizing the composition and structure of cervical tissue, and measuring preterm labor risk. Embodiments of the present invention can use polarization sensitive techniques and properties of cervical tissue, including birefringence, to characterize the structure and composition of a woman's cervix.

In an embodiment, a method can include acquiring in vivo images of cervical tissue, analyzing the in vivo images of the cervical tissue using Mueller matrix polarimetry, and determining one or more parameters of the cervical tissue using the Mueller matrix polarimetry. Birefringence properties of the cervical tissue can be analyzed by decomposing the Muller matrix. Cervical collagen content and organization, percentage of collagen bundles have an elongated or a kinked appearance, dominant angle $\mu$, a concentration parameter $\kappa$, kurtosis (or peakedness), dispersion $\delta$ angles or the distribution of angles (e.g., relative to the cervical canal) of collagen fibers, and extent of cross-linking between collagen fibrils can be determined using the decomposed Muller matrix. The techniques of the present invention can be applied using form birefringence, intrinsic birefringence, or both.

Other parameters that characterize cervical tissue can also be determined, including dispersion of collagen band angles $\theta$ (using circular curtosis, k, as well as the k-parameter, by fitting angular data to a von Mises distribution), collagen density, pyridinoline cross-link concentration, proteoglycan concentration, dominant angle $\mu$ of collagen distribution, depolarization $\Delta$, linear retardance $\delta$ (birefringence), optical rotation R, slow axis orientation $\theta$ (the direction of polarization with the larger optical index) and diattenuation D. Retardation images obtained from the in vivo birefringence measurements can be compared or overlaid with retardation images obtained using polarization sensitive optical coherence tomography (PS-OCT). The maxima, minima, mean, and standard deviation of any or all of the listed parameters can be determined.

As previously discussed, the Mueller matrix can be decomposed to its three canonical matrices (a diattenuator matrix MD, M$\Delta$ accounting for the depolarizing effects of the material, and a retarder matrix MR). The resulting decomposed matrices can be analyzed to yield quantitative medium properties. For example, homogeneity can be determined using the retardation parameter and the angle $\theta$ can be determined, which is directly related to the orientation of the collagenous structures in the tissue.

The in vivo images of embodiments of the present invention can be captured quickly, in 5 seconds or less, and the full cervical imaging can be completed in five minutes or less. Using the captured and processed data from the in vivo images, maps (e.g., an orientation map), graphs, and histograms of the determined parameters (e.g., collagen density and content, collagens structure and organization including kinked and elongated structures, angle of collagen fibers or the distribution of angles relative to the cervical canal, homogeneity, cross-linking, dominant angle $\mu$, concentration parameter $\kappa$, kurtosis or peakedness, and dispersion $\delta$) can be created and displayed on a user interface to illustrate the properties of the cervix and provide a more effective tool for care providers.

In another embodiment, a system can include a camera, a polarization state analyzer having a linear polarizer and one or more variable liquid retarders, and a user interface. The system can also include one or more processors and non-transitory computer readable media with computer executable instructions that can execute the discussed analysis methods.

DETAILED DESCRIPTION

Preterm birth (PTB) is the number one cause of infant neurological disorders, long-term cognitive impairment and other health issues. Numerous factors can lead to PTB. As gestational age advances, the women's cervix becomes "softer" due to a decrease in both pyridinoline cross-link concentration and proteoglycan concentration, which translates into disorganization of collagen in the cervix. To decrease preterm births, it is important to identify at risk pregnancies to initiate preventive interventions.

Embodiments of the present invention are able to monitor and assess collagen content and organization using optical measurements. Embodiments of the present invention can use optical measurements of cervix remodeling during pregnancy to predict the occurrence of pre-term labor. Embodiments of the present invention include a preterm imaging optical system having a standard colposcope with high sensitivity to collagen architecture and content. Embodiments of the present invention can aid in decreasing the number of preterm births by giving physicians the information they need to understand the condition and status of a woman's cervix. Using this information, a physician can formulate a therapeutic strategy, including the use of various medications to delay birth. In turn, this can give infants a few additional weeks of gestation and fundamentally improve the health outcome for both the mother and child.

To decrease preterm births, it is important to identify at risk pregnancies to initiate preventive interventions. Current diagnostics of PTB are based on manual and visual inspection of the cervix to determine dilation, ultrasound for cervical thickness, and fetal fibronectin (FFN) immunoassay. Although spontaneous preterm birth has numerous causes, all result in premature cervical changes, and recent work has highlighted the role of collagen in PTB. The strength of the cervix collagen cross-linked fiber network is integral to the birthing process where forceful contractions in a rigid closed cervix will not result in delivery, while a weak structured cervix will result in preterm birth even if contractions are not present. In addition to collagen, negatively charged glycosyl molecules attached to the collagen can influence water retention and tissue pliability.

Standard clinical methods of assessing PTB include external electronic fetal monitoring (EFM) to determine the presence of uterine contractions, fetal presentation, position, and attitude assessed via Leopold's maneuver, and palpation and evaluation of the maternal abdomen to determine fundal height. Digital evaluation determines the position, consistency, effacement and dilatation of the cervix with a Bishop score often used to assess the probability of PTB. Visual assessment of overt dilatation is done during speculum examination. This also allows for the collection of a fetal fibronectin (FFN) specimen prior to any digital or ultrasound probe of the cervix. Ultrasound imaging is employed to measure cervical length and the presence or absence of funneling of the cervix with transabdominal or vaginal ultrasound. Unfortunately, numerous studies indicate that these methods are insufficient and ineffective in predicting preterm birth.

During the clinical phases of gestation, the cervix function changes from maintaining the fetus within the uterus to an exit canal for delivery. The mechanisms behind cervical changes during pregnancy have been extensively studied, particularly in animal models and to a lesser extent in humans. Clinically, the pregnancy phases are described as cervical softening, ripening, shortening, effacement, dilation and delivery, and recent work has shown how these phases relate strongly to changes in cervical collagen and fibrous tissue directionality and dispersion. About 90% of the human cervix is extracellular connective tissue, of which 55% to 77% is collagen the rest is proteoglycans, glycosaminoglycans, and elastin. The cervical collagen is made of collagen fibrils and proteoglycans influence the size and packing of fibrils into collagen bundles.

Figure 1A:
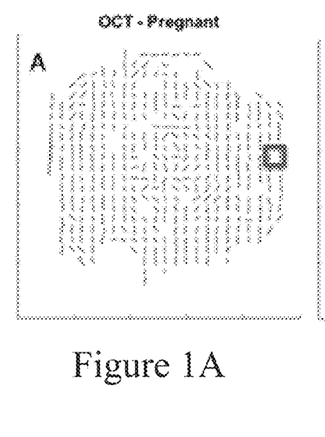
FIG. 1A shows the cervical ultrastructure arrangement of a pregnant woman.
Figure 1B:
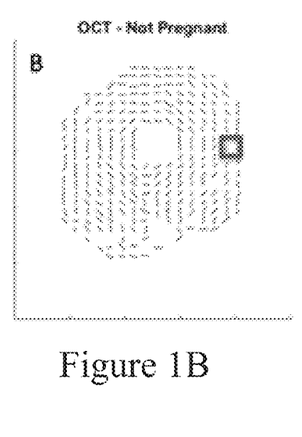
FIG. 1B shows the cervical ultrastructure arrangement of a non-pregnant woman.
Figure 1C:
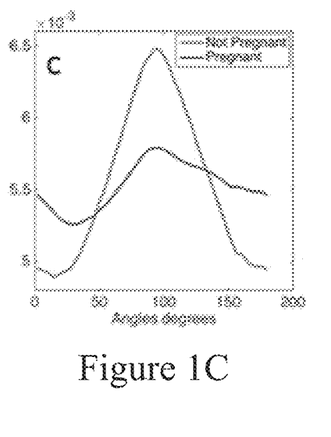
FIG. 1C shows a graph of a typical distribution of cervical fibers for a pregnant woman and a non-pregnant woman in a 1×1 mm area located on the outer edge of the cervix.

During the majority of pregnancy, collagen remains in organized fibrous structures. As gestational age advances, the woman's cervix becomes softer, which translates into dispersion of collagen in the cervix. In pre-term-labor these phases do not change, but their duration is shortened so that the cascade of events leading to parturition is accelerated. Second harmonic generation (SHG) microscopy studies have shown that, during the softening phase, collagen bundles lose their characteristic elongated appearance in favor to a more "kinked" one, and they also become thicker with each gestation day. The cervix contains large bands of circumferential fibers that extend to its outer edge. In non-pregnant women this distinct arrangement is more ordered than during pregnancy, as demonstrated by Gan et al. and illustrated in FIG. 1. Furthermore, while cervical collagen in non-pregnant women (and animals) has a distinct arrangement in a circular form at 90° to the cervical canal, during pregnancy this arrangement is progressively lost as labor approaches.

Embodiments of the present invention can take measurements of collagen dispersion to monitor cervical remodeling in pregnancy. The distribution of angles can be obtained by fitting to a von Mises distribution (the most common circular distribution of angles $$f(\theta | \mu, \kappa) = \frac{e^{\kappa \cos(\theta - \mu)}}{2\pi I_0(\kappa)},$$

wherein Io is the modified Bessel function of order 0). This distribution is based on two parameters, the dominant angle μ, and a concentration parameter κ. κ=0 results in an isotropic distribution while a large K corresponds to a very concentrated distribution about the angle, μ. Circular kurtosis k or peakedness, dispersion δ, and several other statistical methods can be used to describe this effect.

It has been demonstrated that there is a significant difference in dispersion between non-pregnant and pregnant women in the posterior and anterior portion of the cervix. Embodiments of the present invention can utilize the fact that the cervix is composed of structural tissue exhibiting birefringence. Birefringence is the optical property of a material describing the difference in phase velocities experienced by two orthogonally polarized light waves as they traverse the material. Cross-links between collagen fibrils determine the intensity of birefringence. Therefore, a collagen rich environment can be imaged and characterized with polarimetric techniques.

Figure 2A:
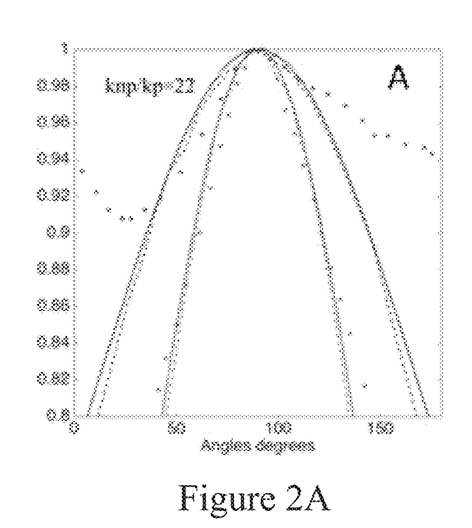
FIG. 2A shows a graph of a von Mises distribution of collagen fiber mimicking pregnant (blue-dashed) and non-pregnant (red-dashed) human tissue.
Figure 2B:
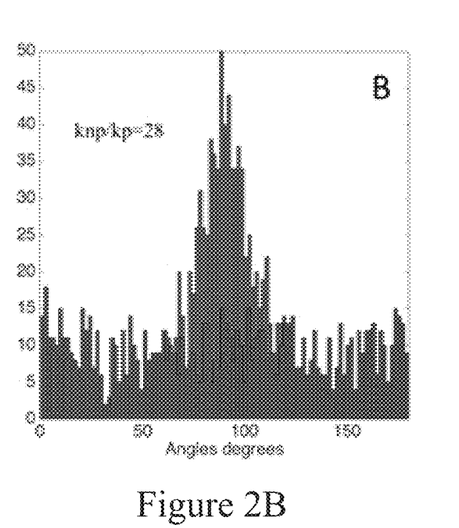
FIG. 2B shows a graph of the polarimetric response to the distribution obtained with a Monte Carlo model and Mueller Matrix decomposition.

Birefringence can arise by the molecular structure of the material (intrinsic birefringence) or the arrangement of microstructures into anisotropic bundles (form birefringence). The cervix possesses both types of birefringence due to the high collagen content and arrangement. Therefore, the fibrous content and dispersion shown in FIG. 2 can be monitored with polarimetric techniques. FIG. 2A shows a graph of a von Mises distribution of collagen fiber mimicking pregnant (blue-dashed) and non-pregnant (red-dashed) human tissue. The solid lines are the fit to a Box Mueller distribution implemented in the Monte Carlo framework. FIG. 2B shows a graph of the polarimetric response to the distribution obtained with a Monte Carlo model and Mueller Matrix decomposition. Quantification of the collagen dispersion through circular curtosis kp for pregnant and knp for non-pregnant show related results.

Mueller matrix imaging can be used in embodiments of the present invention as a polarimetry technique. A 4×4 Mueller matrix (MM) can completely characterize the polarimetric properties of a sample, including its cellular size distribution and refractive index. MM decomposition can be used to extract constituent polarization properties from a Mueller matrix of an unknown complex system. The decomposition of the Mueller matrix yields three canonical matrices $M=M_A M_R M_D$: a diattenuator matrix $M_D$ that includes the effects of linear and circular diattenuation, $M_A$ accounting for the depolarizing effects of the material, and a retarder matrix $M_R$ accounting for the effects of the material linear birefringence and optical activity. Furthermore, the resulting matrices can be analyzed to yield quantitative medium properties that have a demonstrated diagnostic power that can be applied in embodiments of the present invention. These parameters include depolarization Δ, linear retardance δ (birefringence), Optical Rotation R, slow axis orientation θ (the direction of polarization with the larger optical index) and diattenuation D. Of particular importance to the embodiments of the present invention is the angle θ, which is directly related to the orientation of the collagenous structures in the tissue. Different light/tissue interaction mechanisms, such scattering, absorption, chirality, retardation and so on can be isolated by decomposing the MM. Furthermore, the resulting matrices can be analyzed to yield quantitative medium properties that have a demonstrated useful diagnostic power, which can be used in embodiments of the present invention.

Collagen density can be inferred by measuring depolarization, which is the randomization effect on polarized light transmitted through a material. It is measured as a ratio where 0 means there is no effect on the polarization of light transmitted and 1.0 means that the medium fully randomizes transmitted polarized light. Biological tissues are predominantly high scattering which leads to high depolarization values. Less dense tissue generates lower depolarization values and can be seen by treating a collagen-dense sample with collagenase, which metabolizes the protein. Retardation is an important parameter to measure the homogeneities in a sample. A sample that is made of the same materials or has its constituents distributed in the same manner throughout should display the same retardation across the sample. A drastic change in retardation can point to an area having a different material or structure relative the rest of the sample. Orientation images of anisotropic material such as collagen can be produced by computing the retarder axes of the birefringent material. This orientation parameter is calculated from the decomposed $M_R$ and is useful for identifying discrepancies in the ultrastructure arrangement of collagen in tissues where there should be a clear arrangement under physiological norms.

Depolarization is caused by multiple scattering phenomena and is prominent in biological tissue. Depolarization of the cervix can be used to observe changes in the extracellular matrix, shortening and thickening of the collagen bundles and an increase in SHG signal. An example of depolarization is shown in FIGS. 7A through 7D. In FIGS. 7A through 7D, the top images show a healthy baboon heart valve leaflet and the bottom images show a deteriorated baboon heart leaflet.

Figure 7A:
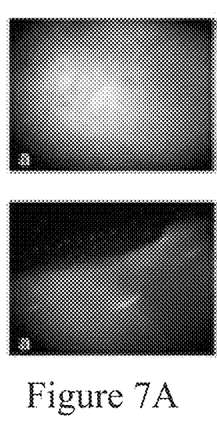
FIG. 7A shows CCD images of a healthy baboon heart leaflet (top) and a deteriorated baboon heart valve leaflet (bottom), captured using an embodiment of the present invention.
Figure 7B:
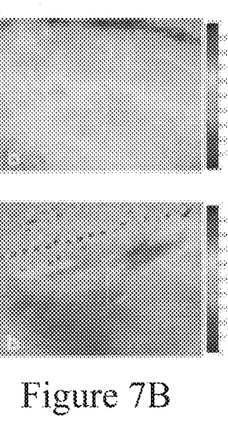
FIG. 7B shows depolarization images of a healthy baboon heart leaflet (top) and a deteriorated baboon heart valve leaflet (bottom), captured using an embodiment of the present invention.
Figure 7C:
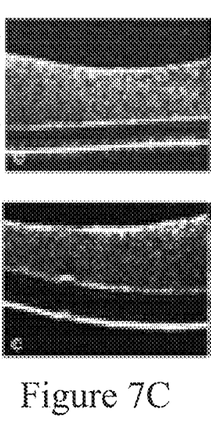
FIG. 7C shows optical coherence tomography (OCT) B-scan images of a healthy baboon heart leaflet (top) and a deteriorated baboon heart valve leaflet (bottom), captured using an embodiment of the present invention.
Figure 7D:
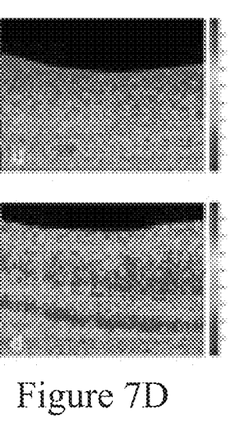
FIG. 7D shows polarization sensitive optical coherence tomography (PS-OCT) images of a healthy baboon heart leaflet (top) and a deteriorated baboon heart valve leaflet (bottom), captured using an embodiment of the present invention.

FIG. 7A shows a CCD image of a healthy baboon heart leaflet (top) and a deteriorated baboon heart valve leaflet (bottom), captured using an embodiment of the present invention. FIG. 7B shows a depolarization image and a polarization sensitive optical coherence tomography (PS-OCT) image of a healthy baboon heart leaflet (top) and a deteriorated baboon heart valve leaflet (bottom), captured using an embodiment of the present invention. FIG. 7C shows an optical coherence tomography (OCT) B-scan image of a healthy baboon heart leaflet (top) and a deteriorated baboon heart valve leaflet (bottom), captured using an embodiment of the present invention. FIG. 7D shows a polarization sensitive optical coherence tomography (PS-OCT) image of a healthy baboon heart leaflet (top) and a deteriorated baboon heart valve leaflet (bottom), captured using an embodiment of the present invention.

Baboon heart valve leaflets comprised primarily of collagen were treated with collagenase, which is known to deteriorate collagen. The effect on the depolarization is highlighted both in the depolarization image and in the polarization sensitive optical coherence tomography (PS-OCT) image of FIG. 7B, showing a strong loss in retardation. Linear retardance can be used to measure the anisotropic organized nature of the cervical collagen. The kinking effect and loss of anisotropy of collagen can be measured with this parameter. The slow axis orientation can be used to point out the main axis orientation of the birefringent bundle.

Figure 8A:
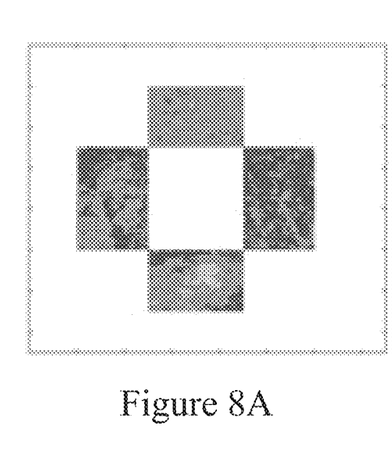
FIG. 8A shows an image of slow axis alignment for a porcine cervix obtained using a Mueller Matrix system according to an embodiment of the present invention.
Figure 8B:
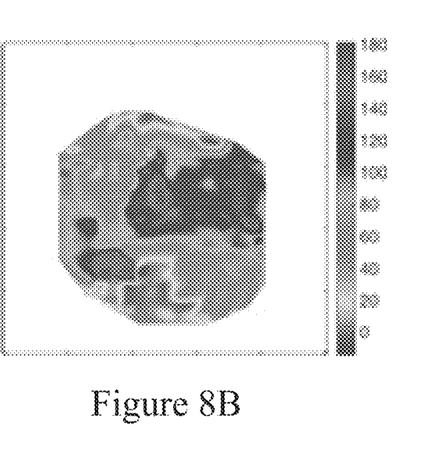
FIG. 8B shows an image of human cervix collagen orientation as measured using optical coherence tomography (OCT).

FIG. 8A shows an image of slow axis alignment for a porcine cervix obtained using a Mueller Matrix system according to an embodiment of the present invention. FIG. 8B shows an image of human cervix collagen orientation as measured by Gan et al. using optical coherence tomography (OCT).

FIG. 8A shows an application of decomposition on cervical tissue including a slow axis image of a porcine cervix obtained using a system according to an embodiment of the present invention. In FIG. 8A it can be seen that a system according to an embodiment of the present invention is capable of distinguishing regions with different collagen alignment. As a comparison, FIG. 8B shows the results obtained by Gan et al. with optical coherence tomography (OCT) on a human non-pregnant cervix. The results have been color coded for comparison, and similar results were also shown by Pierangelo et al. in the healthy human cervix. Optical rotation is caused by the interaction of light with asymmetric optically active chiral molecules like glucose, proteins, and lipids. Diattenuation or dichroism is exhibited by biological molecules such as amino acids and nucleic acids.

Figure 3A:
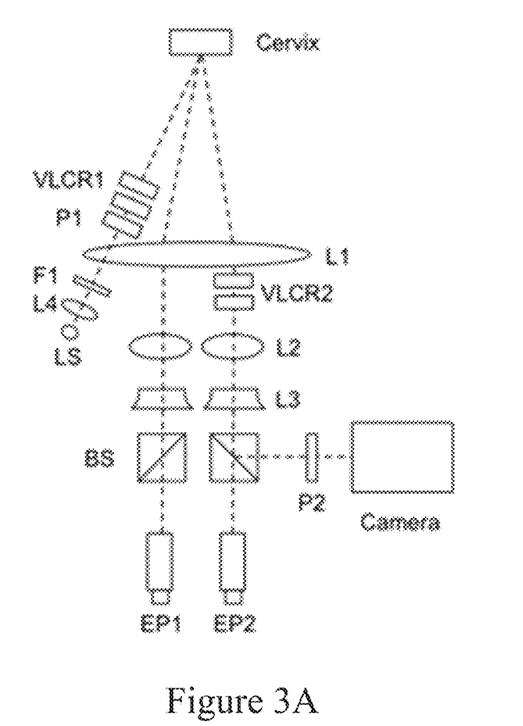
FIG. 3A is a schematic diagram of an imaging system according to an embodiment of the present invention.

Embodiments of the present invention can include graphical user interface (GUI) and a computing system (including a processor, non-transitory computer readable media, volatile and non-volatile memory, software, interfaces, etc.) that can be loaded with images obtained using an imaging system as shown in FIG. 3A. The images can undergo a first phase of analysis (Mueller Decomposition into the d, R, Δ, δ, θ images). The software can prompt the user to find the center of the external os of the cervix, and can automatically mask the os and a circle of about 1 mm from this center. In other embodiments, the software can recommend or identify the cervical os without user input. This step is helpful to avoid image artifacts due to tissue slope. The reviewer can then choose a region of interest (ROI) within one of the images and the system can then automatically calculate maxima, minima, mean, and standard deviation from the mean for all parameters and provide reports including statistical analysis.

In an embodiment of the present invention, images of retardation can be directly correlated to retardation images obtained with PS-OCT. This technique can provide both enface and cross-sectional local retardation, and therefore can be useful in evaluating the Mueller Matrix results (which average the effect of different tissue depths). Furthermore, a PS-OCT system can be co-registered with its own Mueller Matrix polarimeter, and any signal deviation from the PREGOS results will be shown. SHG may have a narrow field of view (500×500 μm) and penetration depth, hence registration with the other modalities can be complex. Nevertheless, SHG information such as collagen bundle distribution and density can be obtained. Furthermore, SHG can provide a clear pictorial representation of collagen, so it can be used to study collagen denaturation and "kinking."

The methods and processes described herein can be embodied as code and/or data. The software code and data described herein can be stored on one or more machine-readable media (e.g., computer-readable media), which may include any device or medium that can store code and/or data for use by a computer system. When a computer system and/or processor reads and executes the code and/or data stored on a computer-readable medium, the computer system and/or processor performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that is capable of storing computer-readable information/data. Computer-readable media should not be construed or interpreted to include any propagating signals. A computer-readable medium of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

The subject invention includes, but is not limited to, the following exemplified embodiments.

Embodiment 1

A method for assessing collagen organization in the cervix OR a method for assessing structure, composition, and organization of cervical tissue OR a method for assessing preterm birth OR a method for assessing the risk of preterm birth OR a method for assessing the condition of a woman's cervix OR a method for assessing the collagen structure of a woman's cervix, the method comprising:
    acquiring in vivo images of cervical tissue;
    applying Mueller matrix (MM) polarimetry (including, for example, 4×4 Mueller matrix polarimetry); and
    determining one or more parameters of the cervical tissue using the Mueller matrix polarimetery.

Embodiment 2

The method of embodiment 1, further comprising analyzing the in vivo images to determine birefringence properties.

Embodiment 3

The method of any of embodiments 1 to 2, further comprising determining collagen content and organization.

Embodiment 4

The method of any of embodiments 1 to 3, further comprising determining what percentage of collagen bundles have an elongated or a kinked appearance.

Embodiment 5

The method of any of embodiments 1 to 4, further comprising determining the angle of collagen fibers, or the distribution of angles (e.g., relative to the cervical canal).

Embodiment 6

The method of any of embodiments 1 to 5, further comprising determining the extent of cross-linking between collagen fibrils.

Embodiment 7

The method of any of embodiments 1 to 6, wherein intrinsic birefringence of the collagen fibrils is used to determine the parameters.

Embodiment 8

The method of any of embodiments 1 to 7, wherein form birefringence of the collagen fibrils is used to determine the parameters.

Embodiment 9

The method of any of embodiments 1 to 8, further comprising determining the dispersion of collagen band angles θ (using circular curtosis, k, as well as the k-parameter by fitting angular data to a von Mises distribution).

Embodiment 10

The method of any of embodiments 1 to 9, further comprising determining collagen density.

Embodiment 11

The method of any of embodiments 1 to 10, further comprising determining pyridinoline cross-link concentration and/or proteoglycan concentration.

Embodiment 12

The method of any of embodiments 1 to 11, further comprising determining the dominant angle μ of collagen distribution.

Embodiment 13

The method of any of embodiments 1 to 12, further comprising determining one or more parameters of depolarization Δ, linear retardance δ (birefringence), optical rotation R, slow axis orientation θ (the direction of polarization with the larger optical index) and diattenuation D.

Embodiment 14

The method of any of embodiments 1 to 13, further comprising correlating retardation images obtained from the in vivo birefringence measurements with retardation images obtained using polarization sensitive optical coherence tomography (PS-OCT).

Embodiment 15

The method of any of embodiments 1 to 14, further comprising calculating maxima, minima, mean, and standard deviation of any or all of the parameters.

Embodiment 16

The method of any of embodiments 1 to 15, further comprising coregistering a PS-OCT image with a Mueller matrix polarimetry image.

Embodiment 17

The method of any of embodiments 1 to 16, further comprising decomposing the Mueller matrix to yield one or more of its three canonical matrices (a diattenuator matrix MD, MΔ accounting for the depolarizing effects of the material, and a retarder matrix MR).

Embodiment 18

The method of any of embodiments 1 to 17, further comprising analyzing the resulting decomposed matrices to yield quantitative medium properties (e.g., the angle θ, which is directly related to the orientation of the collagenous structures in the tissue).

Embodiment 19

The method of any of embodiments 1 to 18, further comprising determining homogeneity using the retardation parameter.

Embodiment 20

The method of any of embodiments 1 to 19, further comprising determining one or more of a dominant angle μ, a concentration parameter κ, kurtosis (or peakedness), and/or dispersion δ.

Embodiment 21

The method of any of embodiments 1 to 20, wherein the in vivo images are captured in 5 seconds or less and/or the full cervical imaging is completed in five minutes or less.

Embodiment 22

The method of any of embodiments 1 to 21, further comprising determining depolarization of the cervical tissues (e.g., to observe changes in the extracellular matrix, shortening and thickening of the collagen bundles and increases in SHG signaling).

Embodiment 23

The method of any of embodiments 1 to 22, further comprising producing one or more maps (e.g., an orientation map, a cervical fiber distribution map, a cervical fiber ultrastructure map, etc.), graphs (e.g., a cervical fiber distribution graph as shown in FIG. 1C, etc.), and/or histograms of the determined parameters (e.g., collagen density and content, collagen structure and organization including kinked structures and elongated structures, angle of collagen fibers or the distribution of angles relative to the cervical canal, homogeneity, cross-linking, dominant angle μ, concentration parameter κ, kurtosis or peakedness, and dispersion δ) to illustrate the properties of the cervix.

Embodiment 101

A system for assessing collagen organization in the cervix OR a system for assessing preterm birth OR a system for assessing the risk of preterm birth OR a system for assessing the condition of a woman's cervix OR a system for assessing collagen structure of a woman's cervix, the system comprising:

a camera, a polarization state analyzer including a linear polarizer, and one or more variable liquid retarders;

a user interface and one or more processors; and a non-transitory computer readable medium containing computer executable instructions that (when executed by a processor) perform a method according to any of Embodiments 1 to 22.

A greater understanding of the present invention and of its many advantages may be had from the following example, given by way of illustration. The following example is illustrative of some of the methods, applications, embodiments and variants of the present invention. They are, of course, not to be considered as limiting the invention. Numerous changes and modifications can be made with respect to the invention.

Example 1

To test the ability of MM polarimetry to relay relevant information of collagen remodeling in PTB, an in-house developed Polarization Sensitive Monte Carlo program and system was created and utilized. The program was thoroughly tested on birefringent phantoms and other Monte Carlo models, as well as highly ordered biological media such as tendon. The model was used to study the back-reflected Mueller Matrix from cervical tissue. In the Monte Carlo model, the birefringent fibers, assumed to be parallel to the surface, were distributed spatially throughout a 1×1×1 cm volume as shown in FIG. 2A, modeled with a Box Muller approximation. The program utilized a 0.5 cm diameter collimated polarized beam of light to illuminate the tissue (optical properties from Drezek et al. [69], $\mu a = 5$ cm$^{-1}$; $\mu s = 180$ cm$^{-1}$) and four different incident states of polarization were launched. Approximately 1e9 photons were used, and the run lasted 20 hours on a cluster of 1500 Intel based cores.

The Monte Carlo returned the Stokes vector of the back-reflected photons from the surface, which was used to calculate the Mueller Matrix. Using Mueller Matrix decomposition, insight was gained on the polarimetrics signature offered by the cervix. In particular, the dominant angle $\mu$ of the collagen distribution was recovered (FIG. 2B), and the dispersion in the collagen was quantified using circular curtosis k as well as the k parameter by fitting this angular data to a von Mises distribution. These simulations demonstrated that polarimetry can be used to relay information of 3D birefringent fiber distribution typical of the cervix, and also demonstrated that Mueller Matrix polarimetry can be used to monitor collagen changes associated with fibers increased angular dispersion.

Figure 3B:
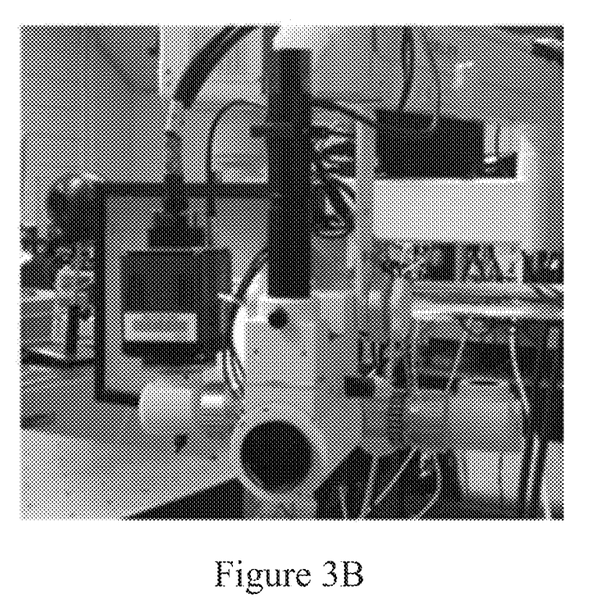
FIG. 3B is a photograph of an imaging system according to an embodiment of the present invention.

A preterm imaging optical system (PREGOS) capable of collecting Mueller Matrix images of the cervix in vivo and in real time was also constructed. The system consisted of a standard colposcope (SEILER 985 Colposcope) modified with polarizing elements, as shown in FIG. 3A and FIG. 3B. That is, FIG. 3A is a schematic diagram of an imaging system according to an embodiment of the present invention, and FIG. 3B is a photograph of an imaging system according to an embodiment of the present invention. As seen in FIG. 3A, a scientific CMOS camera (PCO EDGE 5.5) was combined with a polarization state analyzer (PSA), which included a linear polarizer P2 and two variable liquid crystal retarders VLCR1 and VLCR2 (MEADOWLARK OPTICS). The colposcope had a camera adapter that accommodated the polarizer P2, while the retarders were housed behind the main imaging lens L1 of the colposcope and in front of the eyepieces non-polarizing beam-splitters. The polarization state generator (PSG) included two linear polarizers P1 and P2, and two variable liquid crystal retarders VLCR1 and VLCR2 arranged in a custom support and housed in front of the system light source. A 570 nm filter with a bandwidth of 10 nm full width half max (FWHM) was added to the light source to improve image contrast. Using this wavelength, high sensitivity in scalar retardation and orientation of the birefringence slow axis in the stroma was demonstrated.

The polarimeter had two stages of light modification. The first stage is at the light source for the instrument. Light is first transmitted through a linear polarizer (P1) so that it can be modified using two variable liquid crystal retarders (VLCR1) directly afterwards to create the four different polarization states of light that were used to probe the sample and make up the polarization stage generator (PSG). L1 is a 300 mm focal length lens that focuses light into the eye pieces (EP1/2) and camera port by way of the beam splitters (BS). The LCRs were manufactured to function properly with light between 450-1800 nm and between 0-50° C. Depending on the voltages input into the retarders, polarized light can be rotated into different linear states and have phases introduced between the two directions of linearly polarized light to create elliptical polarization. The light reflected from the sample is then transmitted through a separate pair of LCRs (VLCR2) followed by a linear polarizer (P2) which modifies the returning light into 6 different stages before being captured by a PCO EDGE CMOS camera at 16-bit with a resolution of 2560×2160 pixels and high dynamic range of 88.6 dB.

A 565 nm LED was used as the polarimeter's light source with a bandwidth of 10 nm full width at half maximum and a power of 949 mW. This power output is negligible due to the large area size of illumination, causing little energy deposition on the sample.

Extensive calibration of the system was conducted that showed an error rate of well below 0.1%. Full Mueller Matrix polarimetry (a total of 16 images) was achievable in 3 seconds and focusing was conducted at 60 frames per second. The spatial resolution was 12 µm and field of view was 3 cm. Polarization sensitive silicon based phantoms were constructed to ascertain the ability of the system to recover polarization sensitive parameters and to measure biological media exhibiting birefringence. An example of such testing is shown in FIGS. 4A through 4C, where a polymer and chicken tendon axis orientation were correctly determined.

Figure 4A:
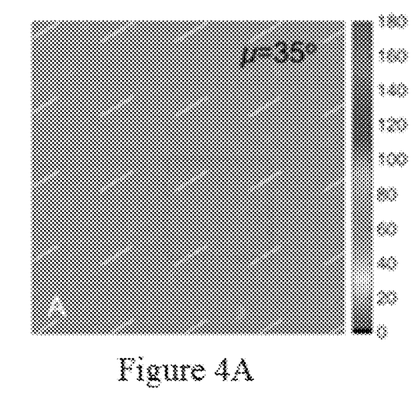
FIG. 4A shows an orientation image of silicon based optical phantoms captured using an embodiment of the present invention.
Figure 4B:
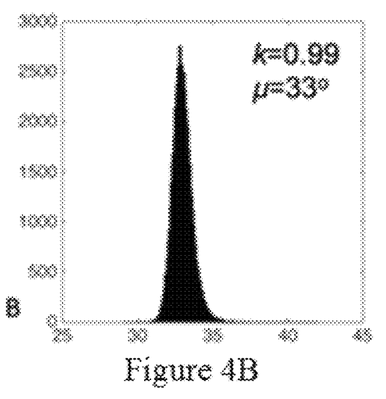
FIG. 4B shows a histogram of the dashed box of the orientation image of FIG. 4A.
Figure 4C:
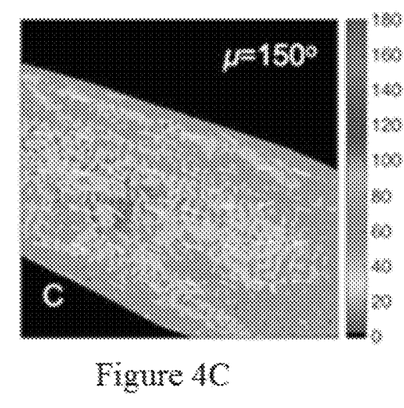
FIG. 4C shows an orientation image of tendon captured using an embodiment of the present invention.
Figure 4D:
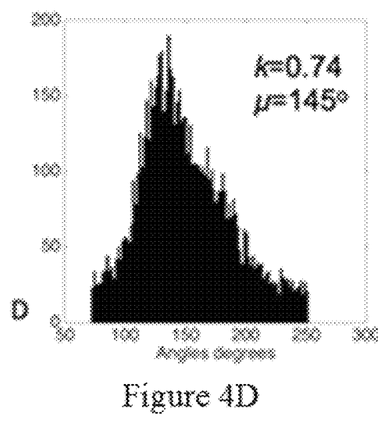
FIG. 4D shows a histogram of the dashed box of the orientation image of FIG. 4C.

FIGS. 4A through 4C display data obtained using Mueller matrix polarimetry. FIGS. 4A and 4B show a silicon phantom with known birefringent orientation, while FIGS. 4C and 4D show tendon, which is made of highly aligned collagen. FIGS. 4A and 4C are orientation images computed from the sample's Mueller matrices with the color bar corresponding to the angle in degrees. FIGS. 4B and 4D are histograms taken from the data selected in the dashed boxes of the orientation images.

Figure 5A:
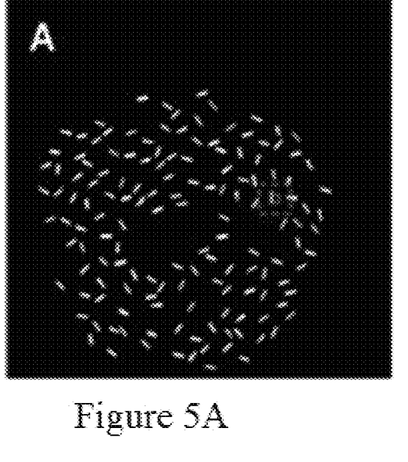
FIG. 5A shows the cervix ultra-structure arrangement of a freshly excised porcine sample captured using an imaging system according to an embodiment of the present invention.
Figure 5B:
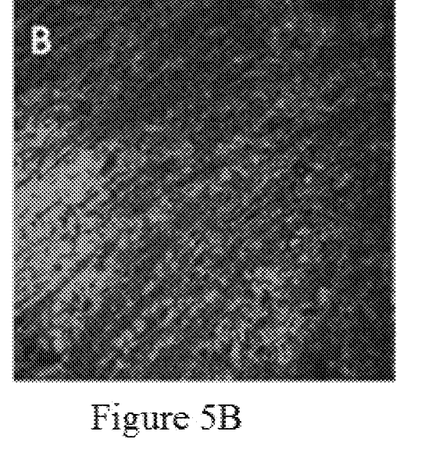
FIG. 5B shows a second harmonic generation (SHG) image of collagen in a 0.5×0.5 mm area (within the square box) of the same cervix shown in FIG. 5A, captured using an imaging system according to an embodiment of the present invention.
Figure 5C:
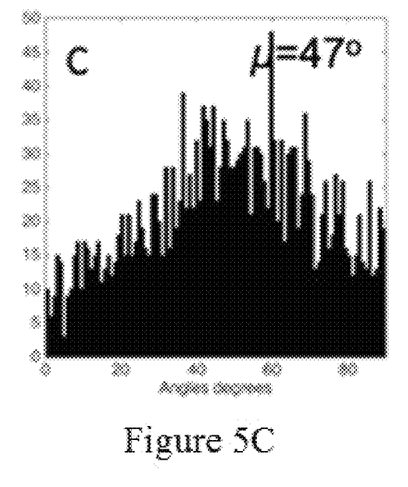
FIG. 5C shows a graph of angular dispersion measured with Mueller Matrix polarimetry (from the boxed portion of the image shown in FIG. 5A) and produced using an imaging system according to an embodiment of the present invention.
Figure 5D:
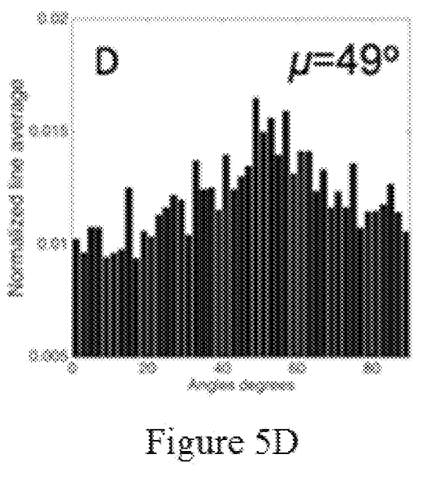
FIG. 5D shows a graph of angular distribution of second harmonic generation imagery obtained using an imaging system according to an embodiment of the present invention.

Extensive tests were also conducted on biological tissue, including porcine cervices, as seen in FIGS. 5A through 5D. FIG. 5A shows the cervix ultra-structure arrangement of a freshly excised porcine sample captured using an imaging system according to an embodiment of the present invention. FIG. 5B shows a second harmonic generation (SHG) image of collagen in a 0.5×0.5 mm area of the same cervix shown in FIG. 5A, captured using an imaging system according to an embodiment of the present invention. FIG. 5C shows a graph of angular dispersion measured with Mueller matrix polarimetry (from a portion of the image shown in FIG. 5A) and produced using an imaging system according to an embodiment of the present invention. FIG. 5D shows a graph of angular distribution of second harmonic generation imagery obtained using an imaging system according to an embodiment of the present invention.

Figure 6:
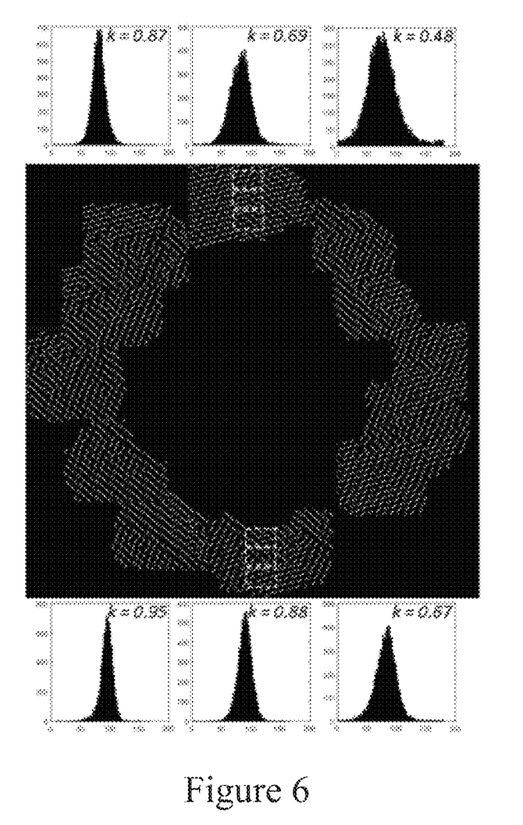
FIG. 6 shows an image and corresponding histograms of fibrous structures within a human cervix captured using a system according to an embodiment of the present invention.

The arrangement of cervical tissues captured during testing showed a typical circular structure, following closely what has been proposed by Myers et al. (as seen in FIG. 1). The results were compared to measurements of the same tissue obtained with a custom second harmonic generation microscope and the image showed a collagen structure with preferential orientation close to ~49 degrees, closely matching the measurements obtained using the experimental system of the present invention. Finally, the system was used to evaluate the cervix of healthy non-pregnant volunteers in a feasibility study, as shown in FIG. 6. That is, FIG. 6 shows an image and corresponding histograms of fibrous structures within a human cervix that were captured using a system according to an embodiment of the present invention. The histograms were derived from sections of the cervix highlighted in white dashed lines. The typical circular structure of cervix collagen was also noticeable in these images. However, only the central portion of the cervix is shown. Full Mueller matrix imagery was achieved in 3 seconds and analysis of data was conducted in post-processing. The angular dispersion was also calculated at various locations, as seen in FIG. 6.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein (including those in the "References" section) are incorporated by reference in their entirety, including all figures and tables, to the extent they are not inconsistent with the explicit teachings of this specification.

REFERENCES

1. Garfield, R. E., et al., *Methods and devices for the management of term and preterm labor*. Ann N Y Acad Sci, 2001. 943: p. 203-24.
2. Pierangelo, A., et al., *Polarimetric imaging of uterine cervix: a case study*. Opt Express, 2013. 21(12): p. 14120-30.
3. Bai, Y., et al., *Dynamic multicomponent engineered tissue reorganization and matrix deposition measured with an integrated nonlinear optical microscopy-optical coherence microscopy system*. J Biomed Opt, 2014. 19(3): p. 36014.
4. Soleimani, F., F. Zaheri, and F. Abdi, *Long-Term Neurodevelopmental Outcomes After Preterm Birth*. Iran Red Crescent *Med J.*, 2014. 16(6): p. e17965.
5. Gan, Y., et al., *Dispersion analysis of collagen fiber networks in cervical tissue using optical coherence tomography*. Photonic Therapeutics and Diagnostics Xii, 2016. 9689.
6. Saiga, 1.S. and L. Doyle, *An overview of mortality and sequelae of preterm birth from infancy to adulthood*. Lancet, 2008. 371(9608): p. 261-269.
7. Kemp, M., et al., *Preterm birth, infection, and inflammation advances from the study of Animal Models*. Reprod Sci 2010. 17: p. 619-628.
8. Goldenberg, R. L., et al., *Epidemiology and causes of preterm birth*. Lancet, Jan. 5, 2008. 371: p. 75-84.
9. Kozuki, N., et al., *The associations of birth intervals with small-for-gestational-age, preterm, and neonatal and infant mortality: a meta-analysis*. BMC Public Health, 2013. 13 Supp 3.
10. Goldenberg, R. L., et al., *Epidemiology and causes of preterm birth*. Lancet, 2008. 371(9606): p. 75-84.
11. Esplin, M. S., *Preterm Birth: A Review of Genetic Factors and Future Directions for Genetic Study*. Obstetrical & Gynecological Survey, 2006. 61(12): p. 800-806.
12. United States. National Office of Vital Statistics., S.D.o.H. United, and CDC, *Vital statistics—special reports*. 2015: Washington. p. 54 v. in.
13. Tielsch, J. M., *Global Incidence of Preterm Birth*. Nestle Nutr Inst Workshop Ser, 2015. 81: p. 9-15.
14. Bloomfield, F., *How is maternal nutrition related to preterm birth?* Annu Rev Nutr., 2011. 31: p. 235-261.
15. Jams, J. D., et al., *The length of the cervix and the risk of spontaneous premature delivery. National Institute of Child Health and Human Development Maternal Fetal Medicine Unit Network*. N Engl J Med, 1996. 334(9): p. 567-72.
16. Foxman, E. F. and P. Jarolim, *Use of the fetal fibronectin test in decisions to admit to hospital for preterm labor*. Clinical Chemistry, 2004. 50(3): p. 663-665.
17. Myers, K., et al., *The mechanical role of the cervix in pregnancy*. J Biomech., 2015.
18. Jams, J. D. and V. Berghella, *Care for Women With Prior Preterm Birth*. Am. J. Obstet. Gynecol., 2010. 203(2): p. 89-100.
19. Feltovich, H., K. Nam, and T. Hall, *Quantitative Ultrasound Assessment of Cervical*. Ultrason Imaging., 2010. 32(3): p. 131-42.
20. Nold, C. M., et al., *Inflammation promotes a cytokine response and disrupts the cervical epithelial barrier: a possible mechanism of premature cervical remodeling and preterm birth*. Am J Obstet Gynecol 2012. 206(208): p. 1-7.
21. Word, R. A., et al., *Dynamics of Cervical Remodeling during Pregnancy and Parturition: Mechanisms and Current Concepts*. Semin Reprod Med 2007. 25(1): p. 069-079.
22. Reiter, E. V. A., K. A. Nielsen, and J. Fedder, *Digital examination and transvaginal scan—competing or complementary for predicting preterm birth?* Acta Obstetricia et Gynecologica Scandinavica, 2012. 91(4): p. 428-438.
23. Bishop, E. H., *Pelvic Scoring for Elective Induction*. Obstet Gynecol, 1964. 24: p. 266-8.
24. Daskalakis, G. J., et al., *Fetal fibronectin as a predictor of preterm birth*. J Obstet Gynaecol, 2000. 20(4): p. 347-53.
25. Albers, L. L., *Monitoring The Fetus In Labor: Evidence to Support the Methods*. The Journal of Midwifery & Women's Health, 2001. 46(6): p. 366-373.
26. Thacker, S. B., D. Stroup, and M. Chang, *Continuous electronic heart rate monitoring for fetal assessment during labor*. Cochrane Database Syst Rev, 2001(2): p. CD000063.
27. Zarko, A., D. Declan, and G. G. M L, *Continuous cardiotocography (CTG) as a form of electronic fetal monitoring (EFM) for fetal assessment during labour*. Cochrane Database of Systematic Reviews, 2013. 5.
28. Honest, H., et al., *Accuracy of cervicovaginal fetal fibronectin test in predicting risk of spontaneous preterm birth: systematic review*. BMJ, 2002. 325(7359): p. 301.
29. Berghella, V., J. K. Baxter, and N. W. Hendrix, *Cervical assessment by ultrasound for preventing preterm delivery*. Cochrane Database Syst Rev, 2009(3): p. CD007235.
30. Garfield, R. E., et al., *Methods and Devices for the Management of Term and Preterm Labor*. Annals of the New York Academy of Sciences, 2001. 943(1): p. 203-224.
31. Zork, N. M., et al., *A systematic evaluation of collagen cross-links in the human cervix*. Am J Obstet Gynecol, 2015. 212(3): p. 321 el-8.
32. Fernandez, M., et al., *Investigating the mechanical function of the cervix during pregnancy using finite element models derived from high-resolution 3D MRI*. Comput Methods Biomech Biomed Engin, 2015: p. 1-14.

33. Myers, K. M., et al., *The mechanical role of the cervix in pregnancy*. J Biomech, 2015. 48(9): p. 1511-23.
34. Akins, M. L., K. Luby-Phelps, and M. Mahendroo, *Second harmonic generation imaging as a potential tool for staging pregnancy and predicting preterm birth (vol 15, 026020, 2010)*. Journal of Biomedical Optics, 2010. 15(3).
35. Read, C. P., et al., *Cervical remodeling during pregnancy and parturition: molecular characterization of the softening phase in mice*. Reproduction, 2007. 134(2): p. 327-40.
36. Kleissl, H. P., et al., *Collagen changes in the human uterine cervix at parturition*. Am J Obstet Gynecol, 1978. 130(7): p. 748-53.
37. Ito, A., et al., *The change in solubility of type I collagen in human uterine cervix in pregnancy at term*. Biochem Med, 1979. 21(3): p. 262-70.
38. Blaustein, A. and R. J. Kurman, *Blaustein's pathology of the female genital tract*. 6th ed. 2011, New York, N.Y.: Springer. xv, 1246 p.
39. Vink, J. and H. Feltovich, *Cervical etiology of spontaneous preterm birth*. Semin Fetal Neonatal Med, 2016. 21(2): p. 106-12.
40. Cunningham, F. G. and J. W. Williams, *Williams obstetrics*. 23rd ed. 2010, New York: McGraw-Hill Medical. xv, 1385 p.
41. Canty, E. G. and K. E. Kadler, *Procollagen trafficking, processing and fibrillogenesis*. J Cell Sci, 2005. 118(Pt 7): p. 1341-53.
42. Granstrom, L., et al., *Changes in the connective tissue of corpus and cervix uteri during ripening and labour in term pregnancy*. Br J Obstet Gynaecol, 1989. 96(10): p. 1198-202.
43. Sennstrom, M. B., et al., *Human cervical ripening, an inflammatory process mediated by cytokines*. Mol Hum Reprod, 2000. 6(4): p. 375-81.
44. Osmers, R., et al., *Glycosaminoglycans in cervical connective tissue during pregnancy and parturition*. Obstet Gynecol, 1993. 81(1): p. 88-92.
45. Straach, K. J., et al., *Regulation of hyaluronan expression during cervical ripening*. Glycobiology, 2005. 15(1): p. 55-65.
46. Romero, R., et al., *The preterm parturition syndrome*. BJOG, 2006. 113 Suppl 3: p. 17-42.
47. Aspden, R. M., *Collagen organisation in the cervix and its relation to mechanical function*. Coll Relat Res, 1988. 8(2): p. 103-12.
48. Zhang, Y., et al., *A compact fiber-optic SHG scanning endomicroscope and its application to visualize cervical remodeling during pregnancy*. Proceedings of the National Academy of Sciences, 2012. 109(32): p. 12878-12883.
49. Chen, X., et al., *Second harmonic generation microscopy for quantitative analysis of collagen fibrillar structure*. Nat Protoc, 2012. 7(4): p. 654-69.
50. Hecht, E., *Optics*. 4th ed. 2002, Reading, Mass.: Addison-Wesley. vi, 698 p.
51. Wang, Z. M., X. Y. Jiao, and X. Xing, [*Tissue engineering of skin*]. Zhongguo Xiu Fu Chong Jian Wai Ke Za Zhi, 2000. 14(4): p. 241-4.
52. Myers, K., et al., *Changes in the biochemical constituents and morphologic appearance of the human cervical stroma during pregnancy*. European Journal of Obstetrics & Gynecology and Reproductive Biology, 2009. 144S: p. S82-S89.
53. Anastasiadou, M., et al., *Polarimetric imaging for the diagnosis of cervical cancer*. physica status solidi (c), 2008. 5(5): p. 1423-1426.
54. Nazac, A., et al., *Optimization of Picrosirius red staining protocol to determine collagen fiber orientations in vaginal and uterine cervical tissues by Mueller polarized microscopy*. Microsc Res Tech, 2015. 78(8): p. 723-30.
55. Lee, S. W., et al., *Optical diagnosis of cervical intraepithelial neoplasm (CIN) using polarization-sensitive optical coherence tomography*. Optics Express, 2008. 16(4): p. 2709-2719.
56. Bancelin, S., et al., *Determination of collagen fiber orientation in histological slides using Mueller microscopy and validation by second harmonic generation imaging*. Opt Express, 2014. 22(19): p. 22561-74.
57. Collier, T., et al., *Sources of scattering in cervical tissue: determination of the scattering coefficient by confocal microscopy*. Appl Opt, 2005. 44(11): p. 2072-81.
58. Carlson, K., et al., *Confocal microscopy: imaging cervical precancerous lesions*. Gynecol Oncol, 2005. 99(3 Suppl 1): p. S84-8.
59. Pierangelo, A., et al., *Multispectral Mueller polarimetric imaging detecting residual cancer and cancer regression after neoadjuvant treatment for colorectal carcinomas*. J Biomed Opt, 2013. 18(4): p. 046014.
60. Dillet, J., et al., *Size determination by use of two-dimensional Mueller matrices backscattered by optically thick random media*. Applied Optics, 2006. 45(19): p. 4669-4678.
61. Lu, S. Y. and R. A. Chipman, *Interpretation of Mueller matrices based on polar decomposition*. Journal of the Optical Society of America a-Optics Image Science and Vision, 1996. 13(5): p. 1106-1113.
62. Wood, M. F., X. Guo, and I. A. Vitkin, *Polarized light propagation in multiply scattering media exhibiting both linear birefringence and optical activity: Monte Carlo model and experimental methodology*. J Biomed Opt, 2007. 12(1): p. 014029.
63. Ghassemi, P., et al., *A new approach for optical assessment of directional anisotropy in turbid media*. J Biophotonics, 2015. 9999(9999).
64. Ghassemi, P., et al., *Out-of-plane Stokes imaging polarimeter for early skin cancer diagnosis*. J Biomed Opt, 2012. 17(7): p. 076014.
65. Ramella-Roman, J. C., et al., *Design, testing, and clinical studies of a handheld polarized light camera*. J Biomed Opt, 2004. 9(6): p. 1305-10.
66. Ramella-Roman, J. C., A. Nayak, and S. A. Prahl, *Spectroscopic sensitive polarimeter for biomedical applications*. J Biomed Opt, 2011. 16(4): p. 047001.
67. Ghassemi, P., et al., *A polarized multispectral imaging system for quantitative assessment of hypertrophic scars*. Biomed Opt Express, 2014. 5(10): p. 3337-54.
68. N I, F., *Statistical Analysis of Circular Data*. Cabridge University Press, 1995.
69. Drezek, R., et al., *Understanding the contributions of NADH and collagen to cervical tissue fluorescence spectra: modeling, measurements, and implications*. J Biomed Opt, 2001. 6(4): p. 385-96.
70. Gan, Y., et al., *Analyzing three-dimensional ultrastructure of human cervical tissue using optical coherence tomography*. Biomedical Optics Express, 2015. 6(4): p. 1090-1108.

What is claimed is:
1. A method for assessing structure, organization, and composition of cervical tissue, the method comprising:

imaging cervical tissue to acquire in vivo images of the cervical tissue;

analyzing the in vivo images of the cervical tissue using Mueller matrix (MM) polarimetry to generate data about the in vivo images of the cervical tissue; and calculating pyridinoline cross-link concentration of the imaged cervical tissue and proteoglycan concentration of the imaged cervical tissue based on the data generated from the MM polarimetry.

2. The method of claim 1, further comprising calculating collagen fiber angles or angle distributions relative to a cervical canal based on the data generated from the MM polarimetry.

3. The method of claim 1, further comprising calculating cross-linking density between collagen fibrils based on the data generated from the MM polarimetry.

4. The method of claim 1, further comprising calculating a dominant angle μ of collagen distribution based on the data generated from the MM polarimetry.

5. A method for assessing structure, organization, and composition of cervical tissue, the method comprising:

imaging cervical tissue to acquire in vivo images of the cervical tissue;

analyzing the in vivo images of the cervical tissue using Mueller matrix (MM) polarimetry;

decomposing the Mueller matrix to yield three canonical matrices including data about the in vivo images of the cervical tissue, the three canonical matrices including a diattenuator matrix MD, a depolarizing effects matrix MΔ, and a retarder matrix MR; and calculating pyridinoline cross-link concentration of the imaged cervical tissue and proteoglycan concentration of the imaged cervical tissue based on the diattenuator matrix MD, the depolarizing effects matrix MΔ, and the retarder matrix MR.

6. The method of claim 5, further comprising generating an orientation image of the cervical tissue based on the diattenuator matrix MD, the depolarizing effects matrix MΔ, and the retarder matrix MR.

7. The method of claim 5, further comprising generating a histogram of an orientation image of the cervical tissue based on the diattenuator matrix MD, the depolarizing effects matrix MΔ, and the retarder matrix MR.

8. The method of claim 5, further comprising performing birefringence measurements of the cervical tissue to obtain first retardation images of the cervical tissue;

using polarization sensitive optical coherence tomography (PS-OCT) on the cervical tissue to obtain second retardation images of the cervical tissue, and correlating the first retardation images obtained from the birefringence measurements with the second retardation images obtained using PS-OCT.

9. The method of claim 5, further comprising calculating one or more parameters of depolarization Δ, linear retardance δ (birefringence), optical rotation R, slow axis orientation θ (the direction of polarization with the larger optical index), and diattenuation D based on the diattenuator matrix MD the depolarizing effects matrix MΔ, and the retarder matrix MR.

10. The method of claim 5, further comprising calculating homogeneity using the retarder matrix MR based on the diattenuator matrix MD, the depolarizing effects matrix MΔ, and the retarder matrix MR.

11. The method of claim 5, further comprising calculating collagen density based on the diattenuator matrix MD, the depolarizing effects matrix MΔ, and the retarder matrix MR.

12. The method of claim 11, further comprising generating a collagen density map based on the diattenuator matrix MD, the depolarizing effects matrix MΔ, and the retarder matrix MR.

13. The method of claim 5, the imaging of the cervical tissue to acquire the in vivo images of the cervical tissue being performed for 5 seconds or less.

14. A method for assessing structure, organization, and composition of cervical tissue, the method comprising:

imaging cervical tissue, using an imaging optical system comprising a colposcope, to acquire in vivo images of the cervical tissue;

analyzing the in vivo images of the cervical tissue using Mueller matrix (MM) polarimetry;

decomposing the Mueller matrix to yield three canonical matrices including data about the in vivo images of the cervical tissue, the three canonical matrices including a diattenuator matrix MD, a depolarizing effects matrix MΔ, and a retarder matrix MR;

calculating pyridinoline cross-link concentration of the imaged cervical tissue and proteoglycan concentration of the imaged cervical tissue based on the diattenuator matrix MD, the depolarizing effects matrix MΔ, and the retarder matrix MR;

calculating birefringence properties of the cervical tissue based on the diattenuator matrix MD, the depolarizing effects matrix MΔ, and the retarder matrix MR;

calculating collagen structure and organization including kinked structures and elongated structures based on the diattenuator matrix MD, the depolarizing effects matrix MΔ, and the retarder matrix MR;

calculating what percentage of collagen bundles have an elongated or a kinked appearance based on the diattenuator matrix MD, the depolarizing elects matrix MΔ, and the retarder matrix MR;

calculating angles of collagen fibers or a distribution of collage fibers angles relative to the cervical canal based on the diattenuator matrix MD, the depolarizing effects matrix MΔ, and the retarder matrix MR; and calculating homogeneity of the cervical tissue based on the diattenuator matrix MD, the depolarizing elects matrix MΔ, and the retarder matrix MR.

* * * * *